US011612329B2

(12) United States Patent
Xie et al.

(10) Patent No.: US 11,612,329 B2
(45) Date of Patent: Mar. 28, 2023

(54) METHOD AND SYSTEM FOR ADJUSTING OUTPUT SIGNAL OF PULSE DIAGNOSIS DEVICE, STORAGE DEVICE, AND CONTROL DEVICE

(71) Applicant: CyberPulse Limited, Hayward, CA (US)

(72) Inventors: Be Xie, Hayward, CA (US); Changhong Yu, Beijing (CN); Haofeng Qin, Beijing (CN)

(73) Assignee: CYBERPULSE LIMITED, Hayward, CA (US)

( * ) Notice: Subject to any disclaimer, the term of this patent is extended or adjusted under 35 U.S.C. 154(b) by 496 days.

(21) Appl. No.: 16/794,816

(22) Filed: Feb. 19, 2020

(65) Prior Publication Data

US 2020/0315469 A1 Oct. 8, 2020

(30) Foreign Application Priority Data

Apr. 2, 2019 (CN) ......................... 201910263290.1
Oct. 23, 2019 (CN) ......................... 201911013967.2

(51) Int. Cl.
*A61B 5/021* (2006.01)
*A61B 5/02* (2006.01)
(Continued)

(52) U.S. Cl.
CPC ...... *A61B 5/02116* (2013.01); *A61B 5/02007* (2013.01); *A61B 5/1075* (2013.01);
(Continued)

(58) Field of Classification Search
CPC ... A61B 5/02; A61B 5/02007; A61B 5/02116; A61B 5/022; A61B 5/1075;
(Continued)

(56) References Cited

U.S. PATENT DOCUMENTS 5,680,867 A * 10/1997 Shimazu .............. A61B 5/7264 600/490
11,064,947 B2 7/2021 Kang et al.
(Continued)

FOREIGN PATENT DOCUMENTS

CN 101978930 A 2/2011
CN 102264287 A 11/2011
(Continued)

OTHER PUBLICATIONS

Chu, Yao, et al. "Human Pulse Diagnosis for Medical Assessments Using a Wearable Piezoelectret Sensing System" 2018. Adv. Funct. Mater., 28 (Year: 2018).*
(Continued)

*Primary Examiner* — Patrick Fernandes
*Assistant Examiner* — Anna Roberts
(74) *Attorney, Agent, or Firm* — Millburn IP PLLC

(57) ABSTRACT

A method for adjusting an output signal of a pulse diagnosis device includes obtaining a pulse signal at a pulse diagnosis region that is acquired by a sensing element of the pulse diagnosis device, and performing a parameter recognition on the pulse signal to obtain a parameter of the pulse signal, and determining a biological structure of the pulse diagnosis region based on the parameter of the pulse signal. The method also includes determining an adjustment factor for the parameter of the pulse signal based on the biological structure, and adjusting the parameter of the pulse signal based on the adjustment factor for the parameter of the pulse signal, to obtain an adjusted pulse signal for the pulse diagnosis region. The pulse signal is a pressure signal applied by an artery in the pulse diagnosis region to an external skin surface corresponding to the artery.

15 Claims, 12 Drawing Sheets

10

1
2
5
6

(51) Int. Cl.
*A61B 5/107* (2006.01)
*A61B 5/00* (2006.01)

(52) U.S. Cl.
CPC .......... *A61B 5/6824* (2013.01); *A61B 5/7271* (2013.01); *A61B 2562/0247* (2013.01); *A61B 2562/043* (2013.01)

(58) Field of Classification Search
CPC ... A61B 5/4854; A61B 5/6824; A61B 5/6843; A61B 5/72; A61B 5/7221; A61B 5/7271; A61B 2562/0247; A61B 2562/043
See application file for complete search history.

(56) References Cited

U.S. PATENT DOCUMENTS

| | | | | |
|---|---|---|---|---|
| 2012/0065525 | A1 | 3/2012 | Douniama et al. | |
| 2018/0325398 | A1* | 11/2018 | Nitzan | A61B 5/02108 |
| 2019/0059825 | A1 | 2/2019 | Baruch | |
| 2019/0282107 | A1* | 9/2019 | Gelissen | A61B 5/02416 |
| 2019/0374112 | A1* | 12/2019 | Kuo | A61B 5/026 |

FOREIGN PATENT DOCUMENTS

| | | | |
|---|---|---|---|
| CN | 106510654 | A | 3/2017 |
| CN | 106725363 | A | 5/2017 |
| CN | 107126201 | A | 9/2017 |
| CN | 108577858 | A | 9/2018 |
| CN | 109288507 | A | 2/2019 |
| CN | 109480804 | A | 3/2019 |
| CN | 110123270 | A | 8/2019 |
| CN | 110786829 | A | 2/2020 |
| WO | 2018001843 | A1 | 1/2018 |

OTHER PUBLICATIONS

International Search Report and Written Opinion dated Jul. 1, 2020, in International Application No. PCT/CN2020/082956, and English machine translation thereof. (18 pages).

* cited by examiner

METHOD AND SYSTEM FOR ADJUSTING OUTPUT SIGNAL OF PULSE DIAGNOSIS DEVICE, STORAGE DEVICE, AND CONTROL DEVICE

CROSS-REFERENCE TO RELATED APPLICATIONS

This application claims priority to Chinese Application No. 201910263290.1, filed on Apr. 2, 2019, and Chinese Application No. 201911013967.2, filed on Oct. 23, 2019, the entire contents of both of which are incorporated herein by reference.

TECHNICAL FIELD

The present disclosure relates to the technology field of medical devices and, more particularly, to a method and a system for adjusting an output signal of a pulse diagnosis device, a storage device, and a control device.

BACKGROUND

Traditional pulse diagnosis is a diagnosis method performed by feeling, through pressing and touching, the pressure applied by arteries located at different parts of a human body to their corresponding external skin surfaces, thereby experiencing and observing changes in the pulse condition. Currently, to reduce the random error introduced by pulse diagnosis by a human being, pulse diagnosis devices have been used to automatically perform the pulse diagnosis. Specifically, a pulse diagnosis device includes a pressure applying device, a pressure acquisition device, and a pressure processing device. The pressure applying device applies an external pressure to a pulse diagnosis region of the human body. The pressure acquisition device detects or measures a pressure at the pulse diagnosis region. The pressure processing device analyzes a pressure signal applied by an artery located as the pulse diagnosis region to an external skin surface based on a detection result obtained by the pressure acquisition device. However, because the placement location of the pressure acquisition device on the wrist of an object to be diagnosed (e.g., a patient), i.e., the biological structure of the pulse diagnosis region, such as the locations and thicknesses of the bone, muscle, and fat layer may have a relatively large difference, such difference may greatly affect the accuracy of an output signal or value of the pulse diagnosis device.

Therefore, there is a need for a method and a system for adjusting (or correcting) the output signal of a pulse diagnosis device to address the above issues in this technical field.

SUMMARY

To address the above issues in the current technologies, i.e., to address the issue of adverse effects on the accuracy of the output signal of the pulse diagnosis device caused by the difference in the biological structures of different wrist portions of the object to be diagnosed, a first aspect of the present disclosure provides a method for adjusting an output signal of a pulse diagnosis device. The method includes: obtaining a pulse signal at a pulse diagnosis region acquired by a sensing element of a pulse diagnosis device; performing a parameter recognition on the pulse signal to obtain one or more parameters of the pulse signal; determining a biological structure of the pulse diagnosis region based on the one or more parameters of the pulse signal; obtaining an adjustment factor for the one or more parameters of the pulse signal based on the biological structure; and adjusting the recognized one or more parameters based on the obtained adjustment factor to obtain an adjusted pulse signal corresponding to the pulse diagnosis region; wherein, the pulse signal is a pressure signal applied by an artery in the pulse diagnosis region to a corresponding external skin surface and acquired by the sensing element.

In an embodiment of the method for adjusting the output signal of the pulse diagnosis device, the step of determining the biological structure of the pulse diagnosis region based on the one or more parameters of the pulse signal includes: based on a predetermined corresponding relationship between predetermined parameter samples and predetermined biological structures, matching to determine a corresponding biological structure based on the recognized one or more parameters of the pulse signal.

In an embodiment of the method for adjusting the output signal of the pulse diagnosis device, obtaining the adjustment factor for the one or more parameters of the pulse signal based on the determined biological structure includes: based on a predetermined corresponding relationship between predetermined biological structure samples and predetermined adjustment factors for the one or more parameters of the pulse signal, matching to determine the adjustment factor corresponding to the one or more parameters of the pulse signal based on the determined biological structure.

In an embodiment of the method for adjusting the output signal of the pulse diagnosis device, the predetermined corresponding relationship between the predetermined biological structure samples and the predetermined adjustment factors for the one or more parameters of the pulse signal is established through the following method: creating multiple simulation models based on multiple predetermined biological structure samples, respectively; determining an elastic modulus of each biological structure sample based on a structural feature of each biological structure sample; based on a predetermined artery pulse force and the elastic modulus corresponding to each biological structure sample, performing a mechanic simulation computation for each simulation model to obtain a value of the artery pulse force at a surface layer structure in each simulation model; and based on each biological structure sample and the value of the artery pulse force at the surface layer structure in each simulation model, determining an adjustment factor corresponding to each biological structure sample.

In an embodiment of the method for adjusting the output signal of the pulse diagnosis device, the biological structure includes a bone, a muscle, a fat, or any combination thereof. The structure feature of the biological structure includes at least one of a location of the biological structure in the pulse diagnosis region and a thickness of the biological structure.

In an embodiment of the method for adjusting the output signal of the pulse diagnosis device, the pulse diagnosis region is a radial artery region.

In an embodiment of the method for adjusting the output signal of the pulse diagnosis device, the one or more parameters of the pulse signal includes at least one of an amplitude and a pressure of the pulse signal.

In an embodiment of the method for adjusting the output signal of the pulse diagnosis device, the sensing element is a pressure sensor array. The at least one of the amplitude and the pressure is at least one of an average value of the amplitudes and an average value of the pressures of multiple output signals of the pressure sensor array. Alternatively, the at least one of the amplitude and the pressure is at least one of a distribution parameter of the amplitudes and a distribution parameter of the pressures of the multiple output signals of the pressure sensor array.

In an embodiment of the method for adjusting the output signal of the pulse diagnosis device, the sensing element is a pressure sensor array. The at least one of the amplitude and pressure is at least one of a maximum value of the amplitudes and a maximum value of the pressures of the multiple output signals of the pressure sensor array.

In a second aspect, the present disclosure provides a method for adjusting an output signal of a pulse diagnosis device. The method includes: obtaining a pulse signal at a radial artery region acquired by a pressure sensor array of the pulse diagnosis device; performing a parameter recognition on the pulse signal to obtain one or more parameters of the pulse signal; based on a predetermined corresponding relationship between predetermined parameter samples and predetermined biological structures, matching to determine a corresponding biological structure based on the one or more parameters of the pulse signal; based on a predetermined corresponding relationship between predetermined biological structure samples and predetermined adjustment factors for the one or more parameters of the pulse signal, matching to determine an adjustment factor for the one or more parameters of the pulse signal based on the matched and determined biological structure; and adjusting the recognized one or more parameters of the pulse signal based on matched and determined adjustment factor for the one or more parameters of the pulse signal, to obtain an adjusted pulse signal corresponding to the pulse diagnosis region; wherein the pulse signal is a pressure signal applied by an artery located at the pulse diagnosis region to an external skin surface corresponding to the artery that is acquired by the pressure sensor array; the biological structure includes a bone, a muscle, a fat, or any combination thereof. A structural feature of the biological structure includes at least one of a location of the biological structure in the pulse diagnosis region and a thickness of the biological structure.

In a third aspect, the present disclosure provides a system for adjusting an output signal of a pulse diagnosis device. The system includes: a signal acquisition module configured to obtain a pulse signal at a pulse diagnosis region acquired by a sensing element of the pulse diagnosis device; a biological structure determination module configured to perform a parameter recognition on the pulse signal to obtain one or more parameters of the pulse signal, and to determine a biological structure of the pulse diagnosis region based on the one or more parameters of the pulse signal; a signal adjustment factor acquisition module configured to obtain a corresponding adjustment factor for the one or more parameters of the pulse signal based on the determined biological structure; and a signal adjustment module configured to adjust the recognized one or more parameters of the pulse signal based on the obtained adjustment factor for the one or more parameters of the pulse signal, to obtain an adjusted pulse signal corresponding to the pulse diagnosis region; wherein, the pulse signal is a pressure signal applied by an artery located at the pulse diagnosis region to an external skin surface corresponding to the artery that is acquired by the sensing element.

In an embodiment of the system for adjusting the output signal of the pulse diagnosis device, the biological structure determination module is configured to determine the biological structure of the pulse diagnosis region based on the following method: based on a predetermined corresponding relationship between predetermined parameter samples and predetermined biological structures, matching to determine a corresponding structural feature of the biological structure based on the one or more parameters of the pulse signal.

In an embodiment of the system for adjusting the output signal of the pulse diagnosis device, the signal adjustment factor acquisition module is configured to obtain the adjustment factor for the one or more parameters of the pulse signal based on the following method: based on a predetermined corresponding relationship between predetermined biological structure samples and predetermined adjustment factors for the one or more parameters of the pulse signal, matching to determine the corresponding adjustment factor for the one or more parameters of the pulse signal based on the determined biological structure.

In an embodiment of the system for adjusting the output signal of the pulse diagnosis device, the predetermined corresponding relationship between the predetermined biological samples and the predetermined adjustment factors for the one or more parameters of the pulse signal is established based on the following method: creating multiple simulation models based on multiple predetermined biological structure samples, respectively; determining an elastic modulus of each biological structure sample based on a structural feature of each biological structure sample; based on a predetermined artery pulse force and the elastic modulus corresponding to each biological structure sample, performing a mechanic simulation computation for each simulation model to obtain a value of the artery pulse force at a surface layer structure in each simulation model; and based on each biological structure sample and the value of the artery pulse force at the surface layer structure in each simulation model, determining an adjustment factor corresponding to each biological structure sample.

In an embodiment of the system for adjusting the output signal of the pulse diagnosis device, the biological structure includes a bone, a muscle, a fat, or any combination thereof. The structure feature of the biological structure includes at least one of a location of the biological structure in the pulse diagnosis region and a thickness of the biological structure.

In an embodiment of the system for adjusting the output signal of the pulse diagnosis device, the pulse diagnosis region is a radial artery region.

In an embodiment of the system for adjusting the output signal of the pulse diagnosis device, the one or more parameters of the pulse signal includes at least one of an amplitude and a pressure of the pulse signal.

In an embodiment of the system for adjusting the output signal of the pulse diagnosis device, the sensing element is a pressure sensor array. The at least one of the amplitude and the pressure is at least one of an average value of the amplitudes and an average value of the pressures of multiple output signals of the pressure sensor array.

In an embodiment of the system for adjusting the output signal of the pulse diagnosis device, the sensing element is a pressure sensor array. The at least one of the amplitude and pressure is at least one of a maximum value of the amplitudes and a maximum value of the pressures of the multiple output signals of the pressure sensor array.

In a fourth aspect, the present disclosure provides a system for adjusting an output signal of a pulse diagnosis device. The system includes: a signal acquisition module configured to obtain a pulse signal at a pulse diagnosis region acquired by a pressure sensor array of the pulse diagnosis device; a biological structure determination module configured to perform a parameter recognition on the pulse signal to obtain one or more parameters of the pulse signal, and to match and determine a corresponding biological structure based on the one or more parameters of the pulse signal, and based on a predetermined corresponding relationship between predetermined parameter samples and predetermined biological structures; a signal adjustment factor acquisition module configured to match and determine a corresponding adjustment factor for the one or more parameters of the pulse signal based on the matched and determined biological structure, and based on a predetermined corresponding relationship between predetermined biological structure samples and predetermined adjustment factors for the one or more parameters of the pulse signal; and a signal adjustment module configured to adjust the recognized one or more parameters of the pulse signal based on the matched and determined adjustment factor for the one or more parameters of the pulse signal, to obtain an adjusted pulse signal corresponding to the pulse diagnosis region; wherein, the pulse signal is a pressure signal applied by an artery located at the pulse diagnosis region to a corresponding external skin surface that is acquired by the pressure sensor array. The biological structure includes a bone, a muscle, a fat, or any combination thereof. A structural feature of the biological structure includes at least one of a location of the biological structure of the pulse diagnosis region and a thickness of the biological structure.

In a fifth aspect, the present disclosure provides a storage device configured to store a plurality of program instructions or codes. The program instructions are loadable and executable by a processor to perform any of the disclosed methods for adjusting the output signal of the pulse diagnosis device.

In a sixth aspect, the present disclosure provides a control device. The control device includes a processor and a storage device. The storage device is configured to store a plurality of program instructions or codes. The program instructions are loadable and executable by the processor to perform any of the disclosed methods for adjusting the output signal of the pulse diagnosis device.

Compared to the conventional technologies, the technical solutions of the present disclosure have at least the following advantages: the disclosed methods for adjusting the output signal of the pulse diagnosis device can match and determine a corresponding adjustment factor for one or more parameters of the pulse signal based on the biological structure of the pulse diagnosis region, and can adjust the pulse signal output by the pulse diagnosis device based on the adjustment factor for the one or more parameters of the pulse signal. As a result, the issue of a relatively large deviation between a pulse signal output by the pulse diagnosis device and an actual pulse signal of the artery in the pulse diagnosis region caused by a relatively large difference between biological structures of different pulse diagnosis regions can be avoided, thereby providing an accurate measurement or detection of a pulse signal of the object to be diagnosed. For example, for a specific object to be diagnosed, when the sensor contacts a region having a relatively thick fat, the pulse signal output by the pulse diagnosis device may be significantly weaker than a pulse signal output by the pulse diagnosis device when the sensor contacts a region having a relatively thin fat. In this situation, the method for adjusting the output signal of the pulse diagnosis device can adjust or correct the pulse signal output by the pulse diagnosis device, such that the pulse signal output by the pulse diagnosis device is as close to the actual pulse signal as possible.

BRIEF DESCRIPTION OF THE DRAWINGS

Detailed embodiments of the present disclosure will be described with reference to the drawings. In the drawings.

DETAILED DESCRIPTION OF THE EMBODIMENTS

In the following descriptions, some embodiments of the present disclosure will be described with reference to the drawings, and in combination of a pulse diagnosis device having a pressure sensor array. A person having ordinary skills in the art can appreciate that these embodiments are only described to explain the technical principles of the present disclosure, and are not intended to limit the scope of the present disclosure. Without deviating from the basic principles of the present disclosure, the technical solutions of the present disclosure can be implemented in a pulse diagnosis device having other types of sensors.

In the description of the present disclosure, “module” and “processor” may include hardware, software, or a combination thereof. A module may include a hardware circuit, various suitable sensors, a communication interface, and/or a storage device, such as a memory. The module may also include a software portion, such as program instructions or codes. In some embodiments, the module may include a combination of software and hardware. The processor may be a central processing unit, a microprocessor, a graphic processing unit, a digital signal processor, or any other suitable processors. The processor may include a function to process the data and/or signals. The processor may be realized as software, hardware, or a combination thereof. A non-transitory computer-readable medium may include any suitable medium that may be configured to store program instructions or codes, such a magnetic disk, a hard disk, an optical disk, a flash memory, a read-only memory, a random-access memory, etc. The phrase “A and/or B” means all possible combinations of A and B, such as A only, B only, or A and B. The phrases “at least one of A or B” and “at least one of A and B” may be interchangeable and may be similar to “A and/or B,” which may include all possible combinations of A and B, such as A only, B only, or A and B. The singular forms of the terms “a,” “the” may also include plural forms.

Figure 1:
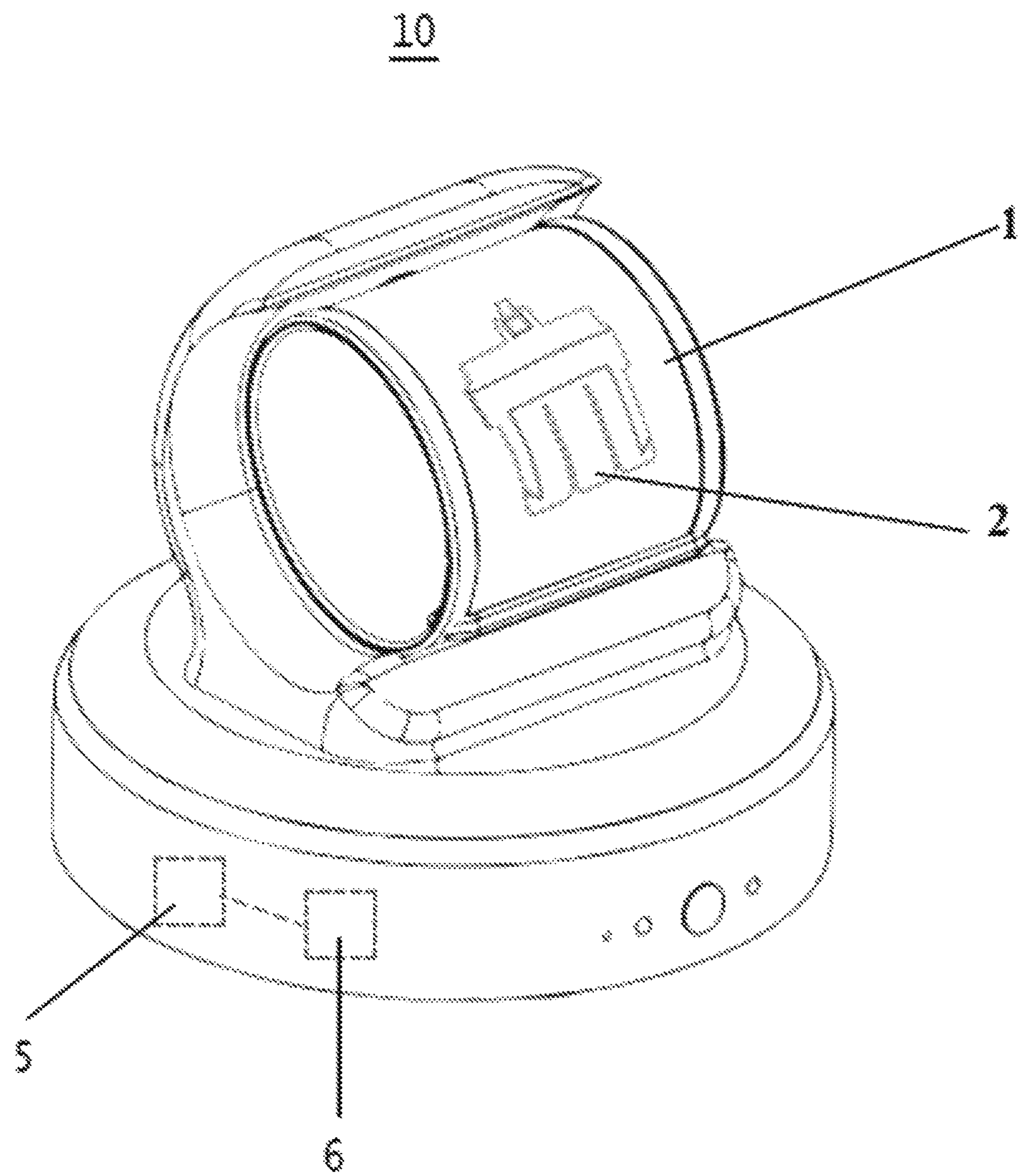
FIG. 1 is a schematic illustration of a pulse diagnosis device, which is an implementation object in which the disclosed technical solution can be implemented.

First, referring to FIG. 1, FIG. 1 is a schematic illustration of a structure of a pulse diagnosis device 10, which is an implementation object in which the technical solutions disclosed in the present disclosure can be implemented. In general, the pulse diagnosis device 10 may include a wristband 1 as a pressure applying device, a sensor 2 as a pressure detection or measurement device, and a processor 5 as a signal processing device. Specifically, in some embodiments, the wristband 1 may include an internally disposed pressure applying bladder or any other suitable pressure applying structure, which may be configured to apply a pre-tension to the wrist of the object to be diagnosed in a circumferential direction, such that the sensor 2 may detect a pulse pressure. The processor 5 may communicate with the sensor 2 to receive pulse pressure signals detected by the sensor 2, and to process the signals. The pulse diagnosis device 10 may also include a memory 6 communicatively connected with the processor 5. The memory 6 may be a non-transitory memory or storage device. The memory 6 may be configured to store computer program codes or instructions configured to realize the methods disclosed herein. The processor 5 may retrieve the computer program instructions from the memory 6 and execute the instructions to realize the methods of the present disclosure. The communication mentioned in the present description can be any suitable wireless or wired communication. In some embodiments, the memory 6 may be configured to store data of the pulse signals detected by the sensor 2. The processor 5 may be configured to retrieve the data of the pulse signals from the memory 6 and process the data.

Figure 2:
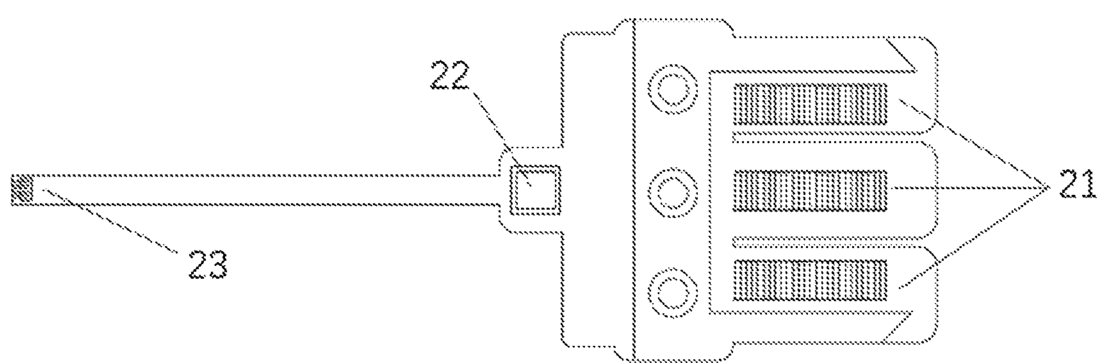
FIG. 2 is a schematic illustration of a sensor array of the pulse diagnosis device.

Next, referring to FIG. 2, FIG. 2 is a schematic illustration of a structure of the sensor 2 of the pulse diagnosis device 10. As shown in FIG. 2, the sensor 2 may be a pressure sensor array (hence the sensor 2 may also be referred to as the pressure sensor array 2). The pressure sensor array may include three sensor arrays 21, a sensor chip 22, and a data interface 23. The pressure sensor array 2 is not limited to three sensor arrays 21. Any suitable number of sensor arrays may be included, such as 1, 2, 4, 5, 6, etc. In some embodiments, each sensor array 21 may include one or multiple pressure sensors. Each pressure sensor may be configured to acquire one or multiple pulse signals. In addition, the detailed types of the pressure sensors are not limited by the present disclosure. For example, the pressure sensors may be piezoelectric pressure sensors. A person having ordinary skills in the art can flexibly select the type of pressure sensors based on actual needs. The sensor chip 22 may be configured to perform an integration or other processing of the signal detected by each pressure sensor. The sensor chip 22 may transmit the processed signal to the processor 5 through the data interface 23 for further processing or direct output. The data interface 23 may be coupled with the processor 5 through a wired connection, or a wireless connection. The data interface 23 may be any suitable wired or wireless interface, such as an Ethernet interface, a WiFi wireless interface, a USB interface, an infrared data transmission interface, etc. In an alternative embodiment, the sensor chip 22 may be integrated with the processor 5, and all data processing may be performed by the processor 5. In such embodiment, the sensor array 21 may directly transmit the detected pulse signals to the processor 5 through the data interface 23 or any other wired or wireless fashion. The sensor chip 22 may include any suitable chip, such as one or more of an electric circuit, a processor (e.g., a microprocessor, a digital signal processor, etc.), a logic gate, etc.

Figure 3:
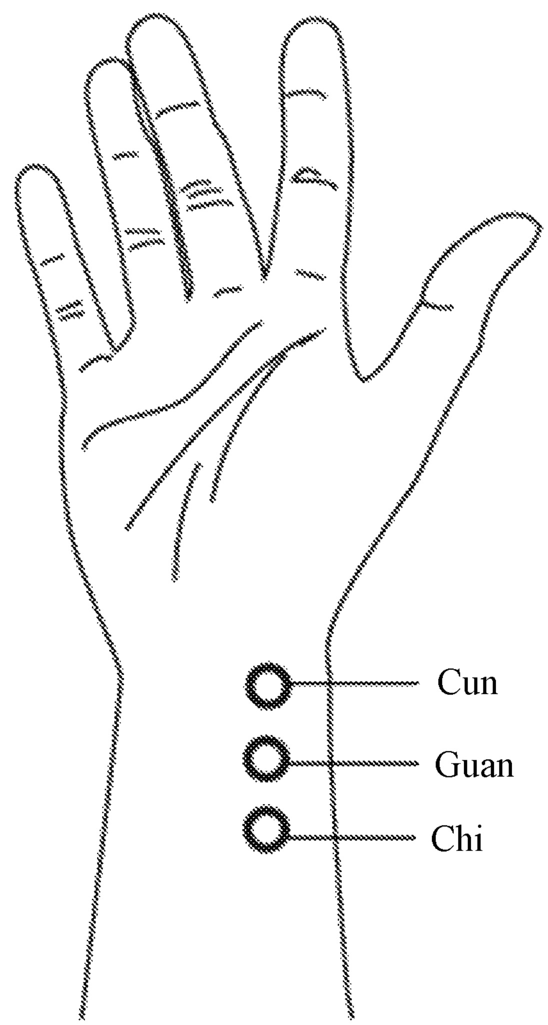
FIG. 3 is a schematic illustration of a wrist of an object to be diagnosed, showing locations of a Cun pulse, a Guan pulse, and a Chi pulse.
Figure 4:
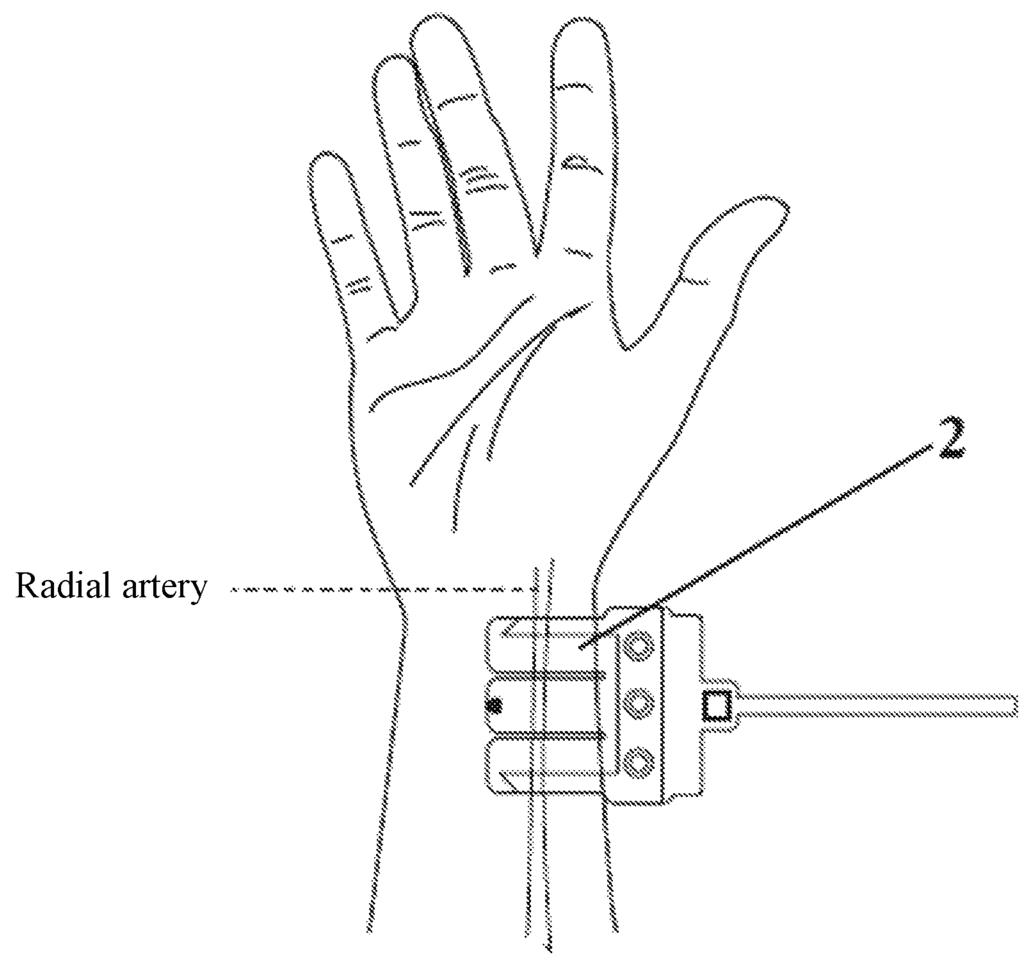
FIG. 4 is a schematic illustration of contact between the sensor array shown in FIG. 2 and the wrist of the object to be diagnosed, showing the radial artery of the object to be diagnosed.

Next, referring to FIG. 3 and FIG. 4, FIG. 3 is a schematic illustration of a wrist of the object to be diagnosed, showing the exemplary locations of the Cun pulse, Guan pulse, and Chi pulse on the radial artery of the object to be diagnosed. FIG. 4 is a schematic illustration of contact between the pressure sensor array 2 shown in FIG. 2 and the wrist of the object to be diagnosed, showing the radial pulse of the object to be diagnosed. As shown in FIG. 4, in a pulse diagnosis process, the three sensor arrays 21 of the sensor 2 may contact the Cun pulse, the Guan pulse, and the Chi pulse of the radial artery of the object to be diagnosed, respectively. In some embodiments, the pulse diagnosis device 10 may not necessarily use all of the three Cun pulse, Guan pulse, and Chi pulse to measure the pulse pressure. Instead, in some embodiments, the pulse diagnosis device 10 may use only one or two of the three pulses. Correspondingly, the sensor 2 may include only one or two sensor arrays 21. In some embodiments, when more (e.g., more than 3) pulses are used to measure the pulse pressure, the sensor 2 may include more (e.g., more than 3) sensor arrays 21.

Figure 5:
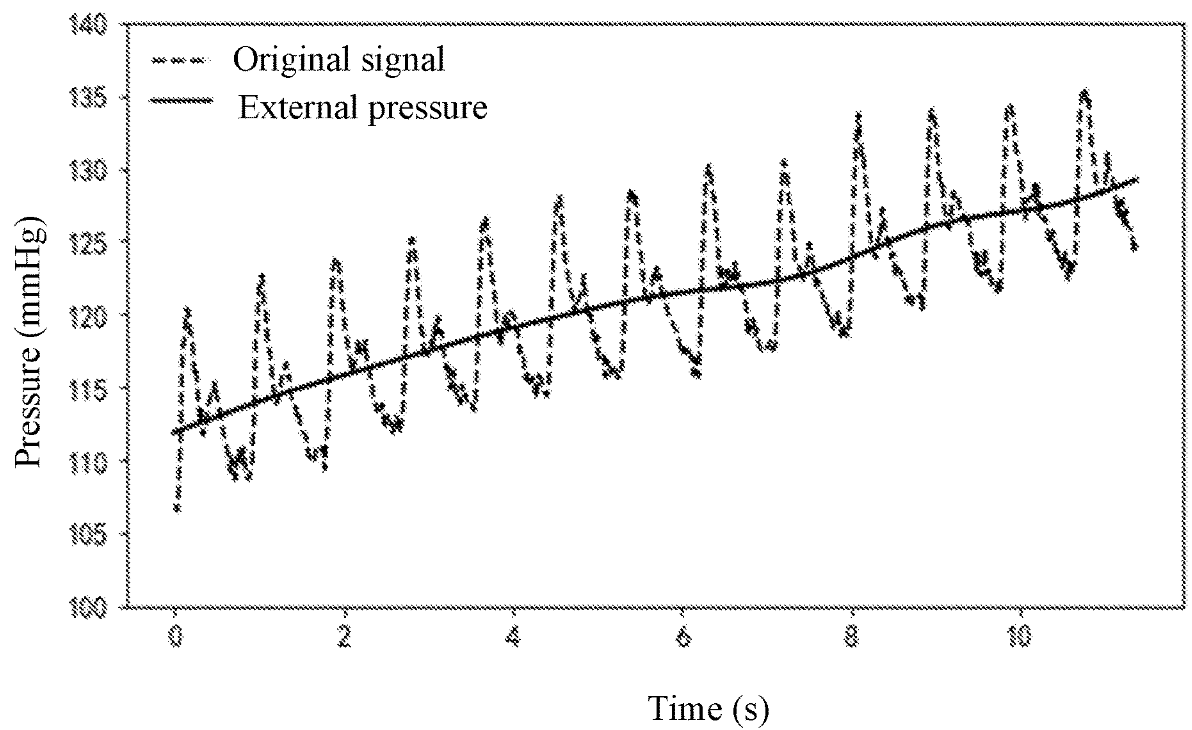
FIG. 5 is a wave plot of an output signal of the pulse diagnosis device, showing both the pulse wave and an external pressure.
Figure 6:
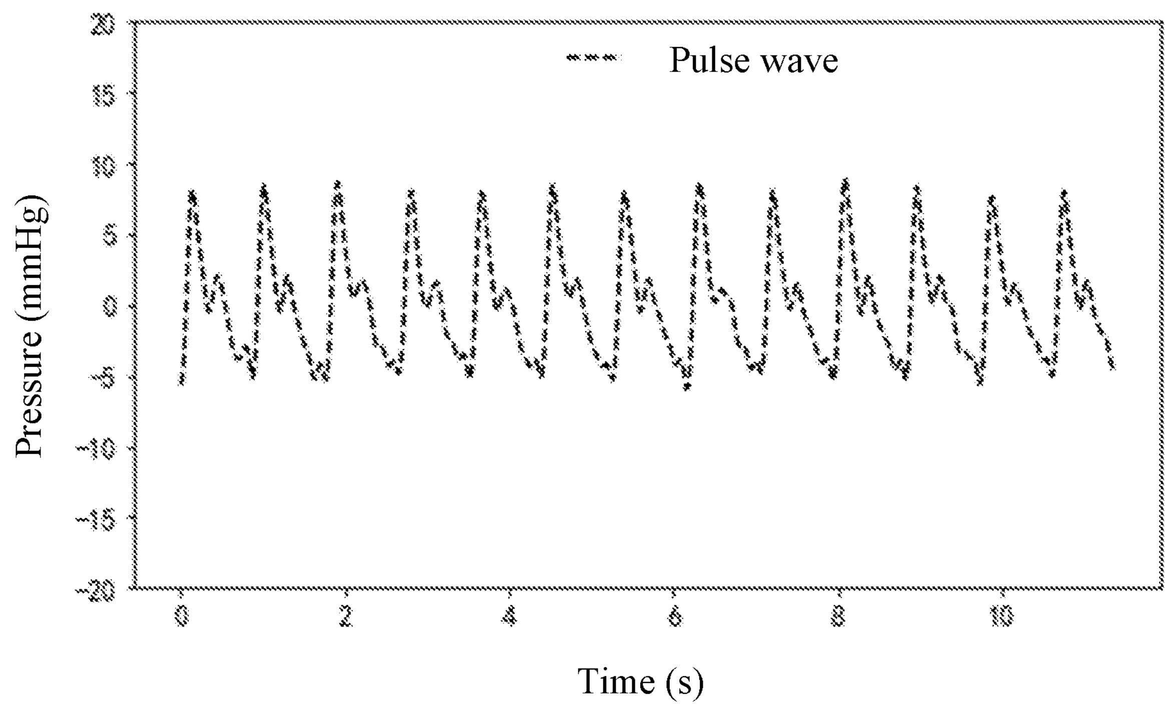
FIG. 6 is another wave plot of another output signal of the pulse diagnosis device, showing only the pulse wave that has been filtered.
Figure 7:
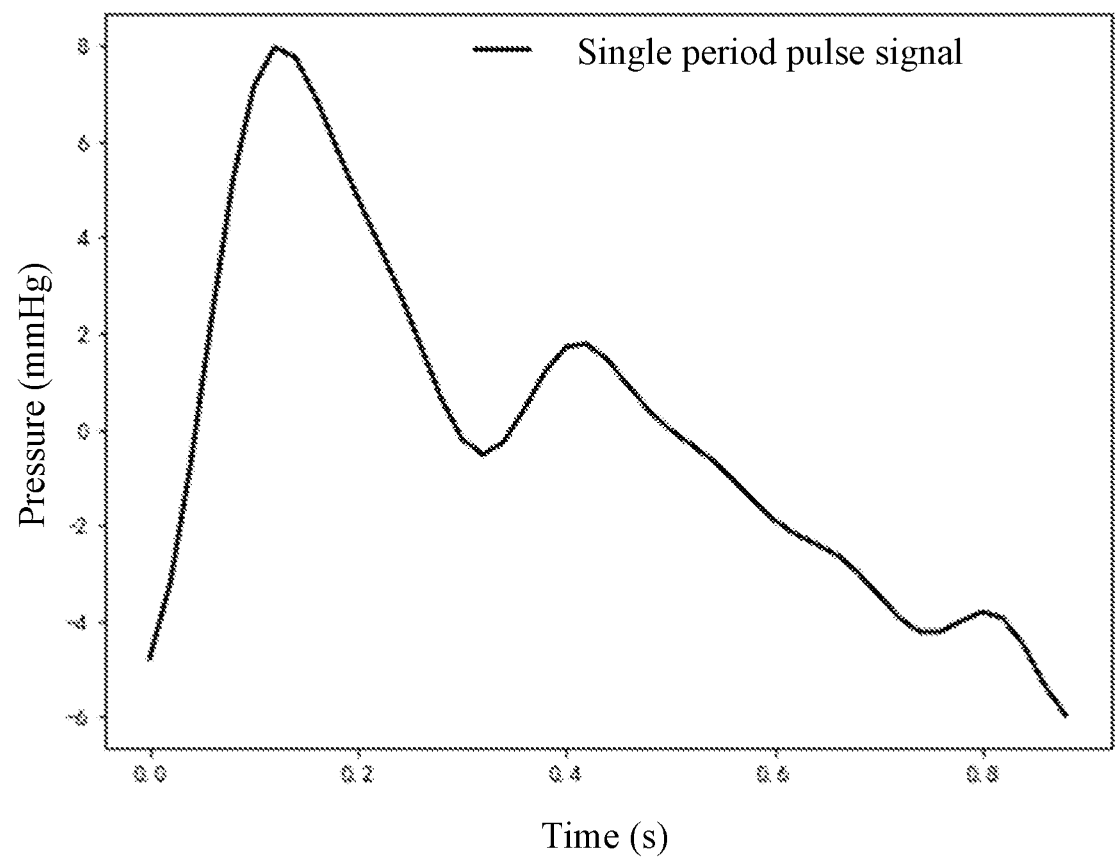
FIG. 7 is an illustrative wave plot of the pulse wave signal corresponding to a single cardiac cycle.

FIGS. 5, 6, and 7 show exemplary pulse signals. These pulse signals may be pressure signals acquired, detected, or measured by the sensor 2, or may be signals obtained after the pressure signals acquired by the sensor 2 have been processed. FIG. 5 shows a wave plot of an output signal of the pulse diagnosis device 10 shown in FIG. 1. FIG. 5 shows both of the pulse signal in a dotted line, and the external pressure signal in a solid line. Specifically, the horizontal axis is time (unit: second), and the vertical axis is pressure (unit: mmHg). The pulse signal and the external pressure signal are both parts of the pressure signal measured by the sensor 2. The pulse wave signal (or pulse signal) is a pressure signal measured by the sensor 2 at the skin of the wrist (e.g., the external skin surface corresponding to the radial artery). The external signal is a pressure signal acquired by the sensor 2, which is applied by the pressure applying device (e.g., the wristband 1) to the wrist skin (e.g., the external skin surface corresponding to the radial artery). The actually measured external pressure may be substantially the same as the specified external pressure that is applied, or may have some difference from the specified external pressure that is applied. The specified external pressure that is applied may be a constant pressure, or may be a pressure that varies with time. Correspondingly, the actually measured external pressure may be a substantially constant pressure, or may be a pressure that varies with time. In some embodiments, when the specified external pressure that is applied is a constant pressure, the actually measured external pressure may also be a substantially constant pressure. When the specified external pressure that is applied varies with time, the actually measured external pressure may also vary with time. For example, as shown in FIG. 5, the actually measured external pressure may gradually increase with time (e.g., substantially linearly increase). In some embodiments, the specified external pressure that is applied and the actually measured external pressure may both decrease with time substantially linearly, or increase or decrease non-linearly. As shown in FIG. 5, the pulse signal may fluctuate substantially around the external pressure signal. As the external pressure changes, the pulse signal measured by the sensor 2 may also change. For example, as shown in FIG. 5, the pulse wave may move upwardly (i.e., increase) as a whole when the external pressure increases. When the external pressure changes with time (e.g., increases with time), the measured pulse signal may change correspondingly as the external pressure changes. Such changes may include, for example, increases in the amplitude of the measured pulse signal, etc. The amplitude used herein may refer to a distance (or difference) between the maximum peak value and the minimum value of the pulse wave signal in a period.

FIG. 6 is another wave plot of the output signal of the pulse diagnosis device 10 shown in FIG. 1, showing only the pulse signal in a dotted line. The pulse signal shown in the dotted line is a result of a filtering process applied to the pressure signal shown in FIG. 5. The filtering process may include filtering the low-frequency portion and the high-frequency portion of the pressure signal. For example, the external pressure signal (low-frequency portion) and the noise (high-frequency portion) of the pressure signal shown in FIG. 5 may have been filtered (e.g., removed). In the wave plot of the pulse signal shown in FIG. 6, the amplitude of each period is the difference between the peak value (a pressure value) and a valley value (a pressure value) in the period. FIG. 7 is a wave plot of the pulse signal corresponding to a single cardiac cycle obtained from the wave plot shown in FIG. 6. In the example shown in FIG. 6, the amplitude corresponding to the first cycle is about 8−(−5) =13 mmHg. In some embodiments, the amplitude of the pulse wave (i.e., a parameter of the pulse signal, amplitude) may refer to an average amplitude or the maximum amplitude of the pulse signal in a predetermined time period. In some embodiments, the amplitude of the pulse wave may be a parameter indicating a distribution of the amplitudes in the pulse diagnosis region, or a parameter indicating a change in the distribution of the amplitudes.

The structure of the pulse diagnosis device that may be an implementation object of the technical solution of the present disclosure and the exemplary waves of the output signal of the pulse diagnosis device are shown and described briefly, such that a person having ordinary skills in the art can be familiar with the implementation scenes of the present disclosure. Next, some embodiments of the present disclosure will be described in detail in the form of flow charts.

Figure 8:
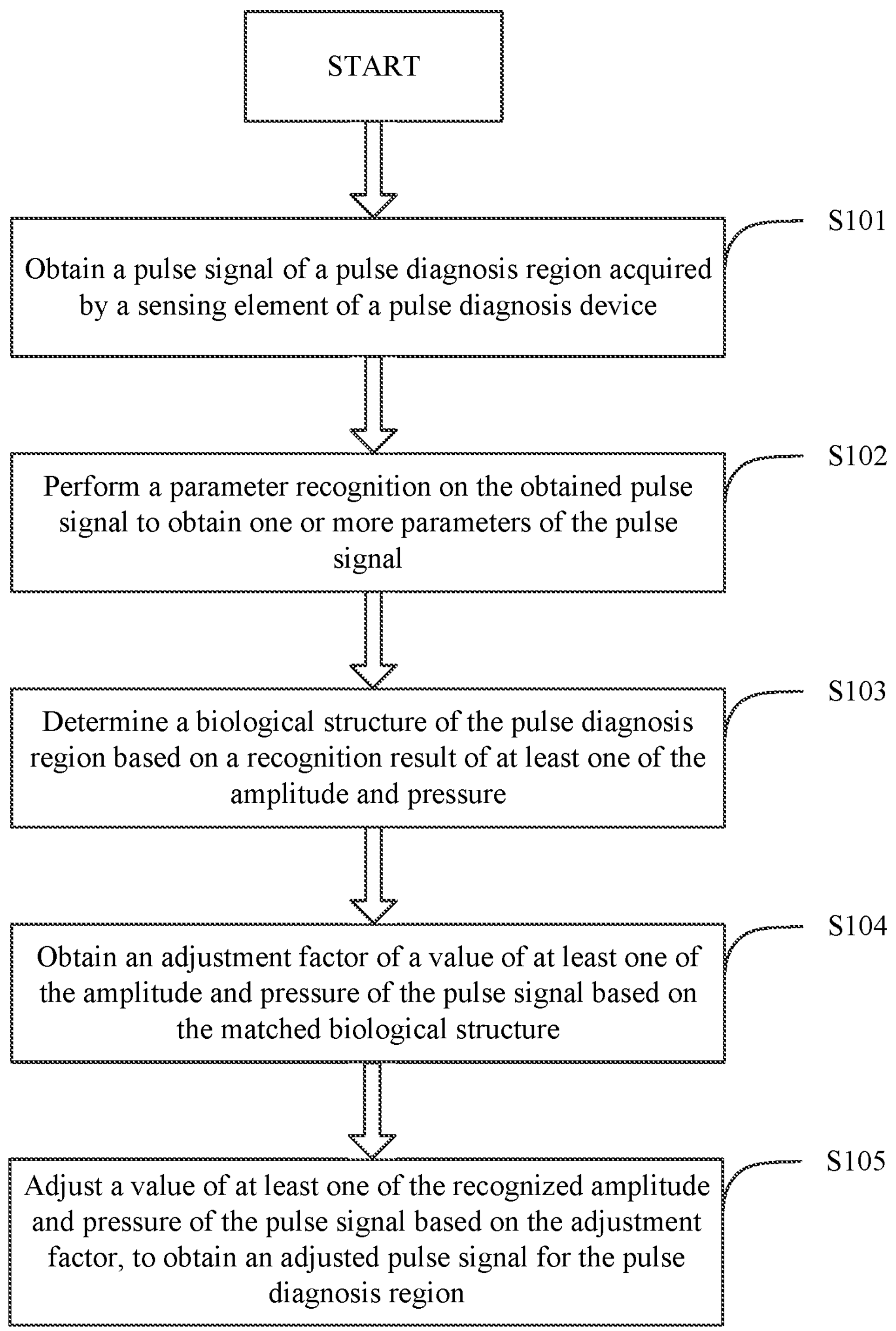
FIG. 8 is a flow chart illustrating primary steps of a method for adjusting an output signal of the pulse diagnosis device, according to an embodiment of the present disclosure.

First, referring to FIG. 8, FIG. 8 is a flow chart showing primary steps of a method for adjusting an output signal of a pulse diagnosis device according to an embodiment of the present disclosure. The method may be executed by the processor 5 of the pulse diagnosis device 10. For example, the program codes or instructions corresponding to the disclosed method may be stored in a non-transitory computer-readable storage medium—such as the memory 6. The processor 5 may be programmed or configured to retrieve the program instructions from the computer-readable medium and execute the program instructions to perform the disclosed methods. It should be noted that although FIG. 8 is described with reference to at least one of the amplitude or the pressure (which are examples of the parameter of the pulse signal) of the pulse signal, this should not limit the scope of the protection of the present disclosure. A person having ordinary skills in the art can adjust the pulse signal based on other parameters of the pulse signal or a combination of other parameters and the amplitude and/or pressure, including, but not limited to, the frequency and the intensity distribution, etc. Such modifications to the disclosed methods for adjusting the output signal of the pulse diagnosis device do not deviate from the basic principles of the present disclosure. Therefore, the modified technical solutions also fall within the scope of protection of the present disclosure. Regarding the amplitude and pressure that are used as the parameters of the pulse signal, it should be noted that both may indicate the strength of the pulse signal. In some embodiments, the pressure as the parameter of the pulse signal may be a pressure at a specific time instance, for example, a pressure at a time instance shown in FIG. 6 (e.g., a pressure at a time instance corresponding to a wave peak, a pressure at a time instance corresponding to a point adjacent the wave peak, etc.). For example, pressures at some time instances corresponding to points adjacent a wave peak may be used as parameters to obtain the amplitude of the pulse signal, or may be individually used as parameters to indicate the strength of the pulse signal. In some embodiments, the pressure as a parameter of the pulse signal may be a maximum pressure or an average value of the absolute values of the pressures within a period (or a time window) or within multiple periods (or multiple time windows), etc. Other pressure related statistic data, such as the median value, the standard deviation of the pressure distribution within a time window, and other parameters indicating the amplitude distribution, other parameters indicating the change in the amplitude distribution, etc., may be used as the parameter of the pulse signal. FIG. 6 shows a pressure with a negative value. The negative value merely indicates a direction. A negative pressure and a positive pressure having the same value (i.e., same absolute value) indicate the same strength of the pressure. For example, in FIG. 6, the amplitude as the parameter of the pulse signal may be a difference between pressure values of a peak and a valley of the pulse signal curve, i.e., a pressure difference. As described above in connection with FIG. 6, the amplitude of the first period is about 8−(−5)=13 mmHg. As a parameter of the pulse signal, the amplitude may be any suitable statistic data of a pulse wave (as shown in FIG. 6), such as an amplitude in a period, an amplitude in a time window, an average value, a maximum value, or other statistic value of multiple amplitudes in multiple periods (or time windows).

Specifically, as shown in FIG. 8, the method for adjusting the output signal of the pulse diagnosis device 10 may primarily include step S101, step S102, step S103, step S104, and step S105. These steps will be described in detail below. The method may be executed or performed by the processor 5 of the pulse diagnosis device 10.

Step S101: obtaining a pulse signal of a pulse diagnosis region acquired by a sensing element of a pulse diagnosis device. In some embodiments, the sensing element may be the pressure sensor array 2 shown in FIG. 2. The pulse signal is a pressure signal applied by an artery in the pulse diagnosis region to an external skin surface corresponding to the artery. For example, when the pulse diagnosis region is a radial diagnosis region, the pulse signal may refer to the pressure signal applied by the radial artery to the external skin surface corresponding to the radial artery as acquired by the pressure sensor array 2. Regarding step S101, it should be noted that the output signal of the pressure sensor array 2 in practice may be a mixed pressure signal. The mixed pressure signal may be a result of dual actions by the external pressure applied by a pressure applying device and the pulse of the object to be diagnosed. In some embodiments, when adjusting the output signal of the pulse diagnosis device 10 based on the disclosed methods, only the pulse signal in the mixed pressure signal may be utilized and the external pressure signal may not be used. Correspondingly, the "pulse signal" in step S101 may not be a signal directly output by the pressure sensor array 2. Instead, the "pulse signal" in step S101 may be a pressure signal that has been processed with a low frequency filter to remove the external pressure signal and with a high frequency filter to remove the noise. In some embodiments, the processor 5 may obtain the pulse signal for the pulse diagnosis region acquired by the pressure sensor array 2 directly from the pressure sensor array 2.

Step S102: performing a parameter recognition on the obtained pulse signal to obtain one or more parameters of the pulse signal. In some embodiments, the one or more parameters of the pulse signal may be the amplitude and/or pressure of the pulse signal. In some embodiments, because the sensing element may be the pressure sensor array 2 having multiple sub-sensors, multiple pulse signals may be detected. In this situation, the method of the present disclosure may include selecting at least one of the amplitudes and pressures from the multiple pulse signals based on a predetermined rule, and then using the at least one of the selected amplitudes and pressures as a recognition result and operational basis for the subsequent steps. In some embodiments, the method may include recognizing at least one of the amplitudes and pressures from all of the pulse signals as the operational basis for the subsequent steps. A person having ordinary skills in the art can appreciate that in the situation in which at least one of the amplitudes and pressures are recognized from all of the pulse signals, the subsequent adjustment operations may take into account the distribution of at least one of the amplitudes and pressures, such that the adjustment result can be more accurate. In the present disclosure, the phrase "at least one of the amplitude(s) and pressure(s)" may indicate amplitude(s) only, pressure(s) only, or both amplitude(s) and pressure(s). When the pressure is used as a parameter to be recognized, the pressure having a corresponding relationship established with the biological structure may be selected as a suitable recognized pressure (which may be the above-described pressure at a certain time instance, a maximum or average pressure within a time window, etc.), or the pressure having a corresponding relationship established with the biological structure may be substantially corresponding to the recognized pressure. For example, if the predetermined corresponding relationship is established between the peak value pressure of the pulse signal and the biological structure, then, when performing a parameter recognition on the detected pulse signal, it may be desirable that the recognized pressure is the peak value pressure. The recognized peak value pressure may be used to inquire a predetermined corresponding relationship to obtain the corresponding biological structure.

In the situation of selecting at least one of amplitudes and pressures of multiple pulse signals detected by the pressure sensor array 2, the method of the present disclosure may significantly reduce the amount of data processing while maintaining the accuracy of the adjustment. For example, when the amplitudes (or pressures) of the multiple pulse signals output by the pressure sensor array 2 are close to one another, it may indicate that the biological structures in the pulse diagnosis regions with which various sensors contact may be similar. The average value (or other suitable statistic data) of the amplitudes or the average value (or other suitable statistic data) of the pressures of the multiple pulse signals output by the pressure sensor array 2 may be used as the recognition result. Alternatively, when the amplitudes (or pressures) of the multiple pulse signals output by the pressure sensor array 2 have relatively large differences, it may indicate that the biological structures of the pulse diagnosis region with which the various sensors contact may have relatively large differences. Then the maximum value of the amplitudes or the maximum value of the pressures of the multiple output signals of the pressure sensor array 2 may be used as the recognition result, such that the amplitude or pressure that serves as the recognition result can better approximate the amplitude or pressure of the actual signal.

In addition, the detailed method for recognizing at least one of the amplitude and pressure of the pulse signal can be any suitable method known in the art, which is not limited by the present disclosure. A person having ordinary skills in the art can select a suitable method to perform the parameter recognition.

Step S103: determining a biological structure of the pulse diagnosis region based on a recognition result of at least one of the amplitude and pressure. In some embodiments, the biological structure of the pulse diagnosis region may be determined based on the following method: based on a predetermined corresponding relationship between predetermined samples of at least one of the amplitudes and pressures and predetermined biological structures, matching to determine a biological structure based on a recognition result of at least one of the amplitude and pressure. That is, at least one of the recognized amplitude and pressure may be used as an index to inquire a pre-established corresponding relationship or mapping relationship between at least one of the amplitudes and pressures and the biological structures to determine the biological structure corresponding to the at least one of the recognized amplitude and pressure.

Specifically, in some embodiments, the biological structure of the pulse diagnosis region may be a bone, a muscle, or a fat (or a combination of any two or all of the three). A structural feature of the biological structure may include at least one of a location and thickness of the biological structure in the pulse diagnosis region. For example, when the pulse diagnosis region is a radial artery region of the wrist of a human body, the structure feature of the biological structure of the radial artery region may include at least one of a location and thickness of the bone, at least one of a location and thickness of the muscle, or at least one of the location and thickness of the fat, or any suitable combination thereof.

More specifically, the corresponding relationship or the mapping relationship between at least one of the amplitudes and pressures and the biological structures may be pre-established through various known methods, including, but not being limited to, repeated experiments or simulation modeling. The former involves using a pulse diagnosis device (e.g., the pulse diagnosis device 10) to actually diagnose the pulses of different objects to be diagnosed or different parts of the wrist of a same object to be diagnosed, and to collect data of at least one of the detected amplitude and pressure. The collected data may be processed to remove noise. The data after noise being removed and the corresponding biological structures may be stored in the form of an inquiry table or a mapping table. In the latter situation, because there are differences in the conductivity of the pulse by different biological structures such as the bone, muscle, and fat, different simulation models may be established with respect to these differences. A predetermined artery pulse force may be applied to these simulation models, and a statistic analysis may be performed on the output results of the pulse signals of the various simulation models. A corresponding relationship between at least one of the amplitudes and pressures of these pulse signals and various simulation models may be saved in the form of an inquiry table or a mapping table. Regarding this aspect, a person having ordinary skills in the art can appreciate that the level of division of the simulation model is determined based on the expected accuracy of signal adjustment. The finer the division of the simulation model, the more accurately the simulation model corresponds to the various different biological structures. Correspondingly, the ultimate adjustment result of the pulse signal can be more accurate.

Step S104: obtaining an adjustment factor of a value of at least one of the amplitude and pressure of the pulse signal based on the matched biological structure. In some embodiments, the adjustment factor of the value of at least one of the amplitude and pressure of the pulse signal corresponding to the biological structure may be obtained through the following method: based on a predetermined corresponding relationship between predetermined biological structure samples and predetermined adjustment factors of the value of at least one of the amplitude and pressure of the pulse signal, matching to determine the corresponding adjustment factor of the value of at least one of the amplitude and pressure of the pulse signal based on the matched biological structure. In other words, the biological structure matched in step S103 may be used as an index to inquire a corresponding relationship or a mapping relationship that is pre-established between the biological structures and the adjustment factors of the values of at least one of the amplitudes and pressures of the pulse signals to determine the corresponding adjustment factor.

Similar to step S103, the corresponding relationship or the mapping relationship between the biological structures and at least one of the values of the amplitudes and pressures of the pulse may be pre-established through various methods, including, but not limited to, repeated experiments or simulation modeling. For example, the former involves using a pulse diagnosis device (e.g., pulse diagnosis device 10) to perform actual pulse diagnoses on objects to be diagnosed who have different biological shapes, to collect detected data of at least one of the amplitude and pressure. The collected data may be processed to remove noise. An adjustment factor for an object to be diagnosed having other biological structures may be calculated based on data of at least one of the amplitude and pressure of an object to be diagnosed having standard biological structures. Finally, the calculated adjustment factors and the corresponding biological structures may be stored in the form of an inquiry table or a mapping table.

Figure 9:
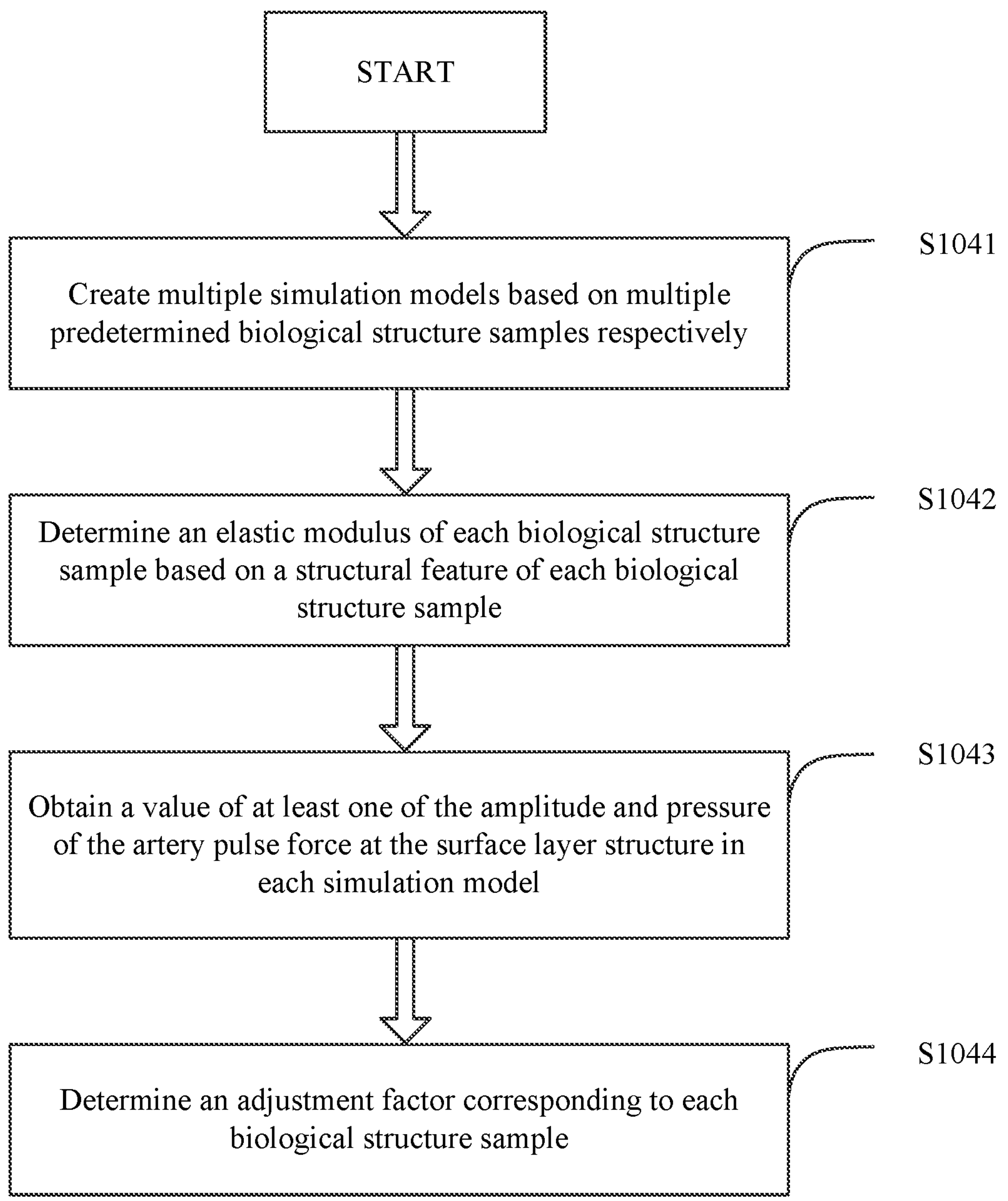
FIG. 9 is a flow chart illustrating a method for establishing a corresponding relationship between biological structure samples and adjustment factors of one or more parameters of the pulse signal.

In some embodiments, the corresponding relationship or the mapping relationship between the biological structures and the adjustment factors for the values of at least one of the amplitudes and pressures may be pre-established through the processes shown in FIG. 9. As shown in FIG. 9, the method for establishing the corresponding relationship between the biological structures and the adjustment factors of at least one of the amplitudes and pressures of the pulse signals may include the following steps.

Step S1041: creating multiple simulation models based on multiple predetermined biological structure samples respectively. As described above, because there are differences in the conductivity of the pulse by different biological structures, such as the bone, muscle, and fat, the simulation models established for different biological structures may be different. Similarly, the level of division between the biological structure samples and the simulation models may be dependent on the expected accuracy of the signal adjustment. The finer the division of the simulation models, the more accurately the simulation models correspond to the different biological structures encountered in actual practices. Correspondingly, the final adjustment result of the pulse signal is more accurate.

Step S1042: determining an elastic modulus of each biological structure sample based on a structural feature of each biological structure sample. Because different biological structures such as bone, muscle, and fat have different elastic moduli, the conductivities of the pulse by these different biological structures may have differences. The calculated elastic moduli of the various biological structure samples may form the bases for subsequent simulation computations. In addition, the elastic modulus of each biological structure sample may be determined through any suitable manner, including actual measurement, setting based on actual experience, indirectly derived based on experimental results, etc., which is not limited by the present disclosure.

Step S1043: based on a predetermined artery pulse force and the elastic modulus corresponding to each biological structure sample, performing a mechanic simulation computation for each simulation model to obtain a value of at least one of the amplitude and pressure of the artery pulse force at the surface layer structure in each simulation model. As an example, the simulation model may be created as a function having independent variables including at least one of the location and thickness of each biological structure sample and the type (e.g., bone, muscle, or fat) of each biological structure sample, and having a dependent variable that is at least one of the amplitude and pressure. For a given artery pulse force, when at least one of the type variable, location variable, and thickness variable for each biological structure sample is input to the simulation model, the value of at least one of the amplitude and pressure of the artery pulse force at different thickness of the biological structure sample can be calculated in each simulation model. This is the above-referenced mechanic simulation computation. Correspondingly, when the thickness independent variable is the thickness of the surface layer structure, a result of the mechanic simulation computation is the value of at least one of the amplitude and pressure of the artery pulse force at the surface layer structure in the simulation model. The above function is merely an example. A person having ordinary skills in the art can create other types of simulation model based on actual needs. The detailed form of the simulation model does not limit the scope of the protection of the present disclosure.

Step S1044: determining an adjustment factor corresponding to each biological structure sample based on each biological structure sample and a value of at least one of the amplitude and pressure of the artery pulse force at the surface layer structure in a corresponding simulation model. Similar to the repeated experiments operation method, after obtaining each biological structure sample and a value of at least one of the amplitude and pressure of the artery pulse force at the surface layer structure in the corresponding simulation model, adjustment factors of other biological structure samples may be calculated based on data of at least one of the amplitude and pressure of a standard biological structure sample. Finally, the calculated adjustment factors and the corresponding biological structure samples are stored in the form of an inquiry table or a mapping table.

Referring to FIG. 8, the method shown in FIG. 8 also includes step S105: adjusting a value of at least one of the recognized amplitude and pressure of the pulse signal based on the adjustment factor of at least one of the amplitude and pressure, to obtain an adjusted pulse signal for the pulse diagnosis region. Specifically, in some embodiments, multiplying the value of at least one of the amplitude and pressure recognized in step S102 by the adjustment factor determined in step S104 may result in an adjusted value of at least one of the amplitude and pressure. The pulse signal having the adjusted value of at least one of the amplitude and pressure is an adjusted pulse signal. It should be noted that as described in connection with FIG. 5, because the amplitude and pressure of the pulse signal may change as the external pressure changes, the method for adjusting the pulse signal shown in FIG. 8 typically refers to the situation when the external pressure is specified. The specified external pressure may be an external pressure of a specific value, or may be an external pressure having a value in a specific range. In addition, in this range, the amplitude of the pulse signal may be substantially constant over time. In other words, the variation in the amplitude may be small over time, e.g., smaller than a predetermined value. The pressure may also maintain substantially constant wave shapes and values. That is, the variable in the wave shape of the pressure may be small over time, e.g., smaller than a predetermined value. In some embodiments, the variation in the statistic value of the pressure that is used (e.g., the average value, the maximum value, the minimum value, etc.) is small over time, e.g., smaller than a predetermined value. In the pulse wave shown in FIG. 6, the amplitude and pressure, which are parameters of the pulse wave, maintain substantially constant over time.

In some embodiments, when the pulse diagnosis region is the radial artery region, in the method for adjusting the output signal of the pulse diagnosis device 10 as shown in FIG. 8, prior to executing step S101, the method also includes: obtaining a center line of the radial artery and a Cun pulse location, a Guan pulse location, and a Chi pulse location of the radial artery, and determining a pulse signal acquisition region, i.e., the pulse diagnosis region, based on the center line of the radial artery, the Cun pulse location, the Guan pulse location, and the Chi pulse location, such that the pulse signals in the pulse diagnosis region may be acquired by the sensing element of the pulse diagnosis device 10.

Specifically, referring back to FIG. 4, because the sensing element of the pulse diagnosis device 10 is a pressure sensor array, the method for adjusting the output signal of the pulse diagnosis device 10 as shown in FIG. 8 may include the following steps for obtaining the center line of the radial artery: first, in a direction substantially perpendicular to the radial artery, obtaining location information of a pressure sensor in each row or column of pressure sensors included in the pressure sensor array that detects the largest pulse signal. Then, determining a center line location of the radial artery based on the obtained location information. Specifically, connecting the locations of three pressure sensors that have detected the largest pulse signals in the three rows or columns of pressure sensors included in the pressure sensor array, to obtain the center line location of the radial artery.

Figure 10:
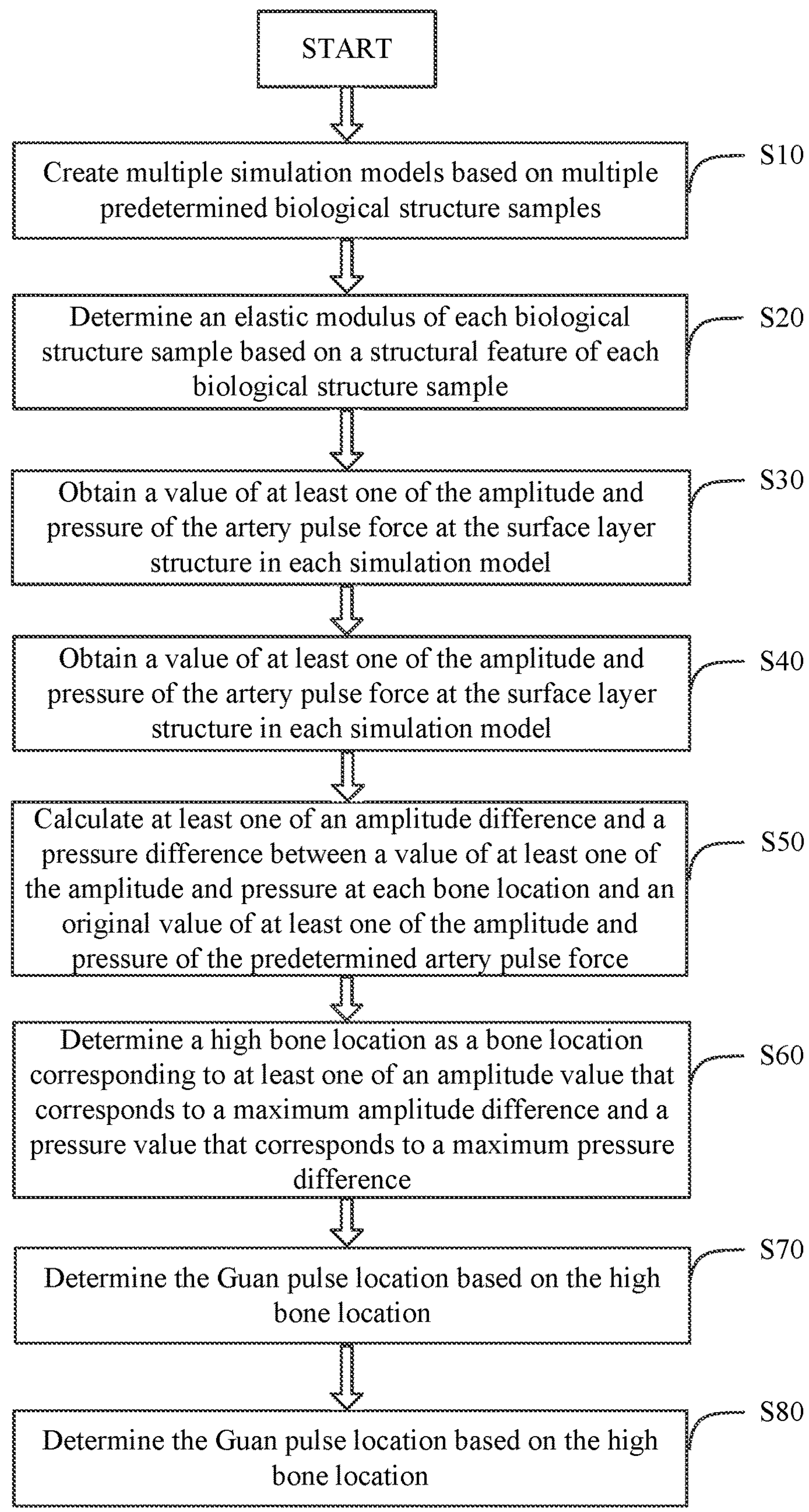
FIG. 10 is a flow chart illustrating a method for determining the Cun pulse location, the Guan pulse location, and the Chi pulse location of the radial artery.

More specifically, the method for adjusting the output signal of the pulse diagnosis device 10 as shown in FIG. 8 may include steps shown in FIG. 10 to obtain the Cun pulse location, Guan pulse location, and Chi pulse location of the radial artery as shown in FIG. 3. In some embodiments, the method shown in FIG. 10 may be executed by the processor 5 of the pulse diagnosis device 10. For example, the program instructions or codes corresponding to this method may be stored in a non-transitory computer-readable storage medium. The processor 5 may be programmed or configured to retrieve the program instructions from the computer-readable medium and execute the program instructions to perform the method. In some embodiments, the method shown in FIG. 10 may be partially executed by the processor 5, and partially executed by another processor. For example, the portions executed by the processor 5 may include steps S40 to S80, and may not include steps S10 to S30.

Step S10: creating multiple simulation models based on multiple predetermined biological structure samples. The biological structure samples may include at least one of a location and thickness of the bone in the radial artery region, at least one of the location and thickness of the muscle in the radial artery region, or at least one of the location and thickness of the fat in the radial artery region, or any suitable combination thereof. As described above, because there are differences in the conductivities of the pulse by different biological structures such as bone, muscle, and fat, the simulation models created for different biological structures may be different.

Step S20: determining an elastic modulus of each biological structure sample based on a structural feature of each biological structure sample. Any suitable method may be used to determine the elastic modulus of each biological structure sample, including actual measurement, setting based on experience, or deriving indirectly based on experimental results, etc., which is not limited by the present disclosure.

Step S30: based on a predetermined artery pulse force and the elastic modulus corresponding to each biological structure sample, performing a mechanic simulation computation on each biological model to obtain a value of at least one of the amplitude and pressure of the artery pulse force at the surface layer structure in each simulation model. As an example, the simulation model may be created as a function having independent variables including at least one of the location and thickness of each biological structure sample and the type (e.g., bone, muscle, or fat) of each biological structure sample, and having a dependent variable that is at least one of the amplitude and pressure. For a given artery pulse force, when at least one of the type variable, location variable, and thickness variable for each biological structure sample is input to the simulation model, the value of at least one of the amplitude and pressure of the artery pulse force at different thickness of the biological structure sample can be calculated in each simulation model. This is the above-referenced mechanic simulation computation. Correspondingly, when the thickness independent variable is the thickness of the surface layer structure, a result of the mechanic simulation computation is the value of at least one of the amplitude and pressure of the artery pulse force at the surface layer structure in the simulation model. The above function is merely an example. A person having ordinary skills in the art can create other types of simulation model based on actual needs. The detailed form of the simulation model does not limit the scope of the protection of the present disclosure.

Step S40: obtaining a value of at least one of the amplitude and pressure at each bone location in the radial artery region. Specifically, the computation results from step S30 may be filtered using bone as a structural feature index, to obtain a value of at least one of the amplitude and pressure at each bone location in the radial artery region.

Step S50: calculating at least one of an amplitude difference and a pressure difference between a value of at least one of the amplitude and pressure at each bone location and an original value of at least one of the amplitude and pressure of the predetermined artery pulse force.

Step S60: determining a high bone location as a bone location corresponding to at least one of an amplitude value that corresponds to a maximum amplitude difference and a pressure value that corresponds to a maximum pressure difference.

Step S70: determining the Guan pulse location based on the high bone location. Specifically, because there is a corresponding relationship between the high bone location and the Guan pulse location in the radial artery region, the Guan pulse location may be obtained based on the high bone location and this corresponding relationship.

Step S80: determining the Cun pulse location and the Chi pulse location based on the Guan pulse location. Likewise, because there is a corresponding relationship between the Guan pulse location and the Cun pulse location and Chi pulse location in the radial artery region, the Cun pulse location and the Chi pulse location may be obtained based on the Guan pulse location and this corresponding relationship.

It should be noted that although the various steps of the above embodiments are described in a specific order, a person having ordinary skills can appreciate that to realize the effect of the present disclosure, different steps may not necessarily be executed in the described order. The steps may be simultaneously executed (e.g., executed in parallel) or may be executed in other orders. Such variations are also within the scope of protection of the present disclosure.

Based on the above embodiments of the disclosed method, the present disclosure also provides a system 200 for adjusting an output signal of the pulse diagnosis device 10. The system 200 for adjusting the output signal of the pulse diagnosis device 10 will be described below with reference to FIG. 11. The system 200 for adjusting the output signal of the pulse diagnosis device 10 may be included as a portion of the pulse diagnosis device 10 shown in FIG. 1. In some embodiments, the system 200 may be an independent system that is connected (e.g., remotely connected) with the pulse diagnosis device 10, and configured to process data or signals transmitted from the pulse diagnosis device 10 and to transmit the processing result to the pulse diagnosis device 10.

Figure 11:
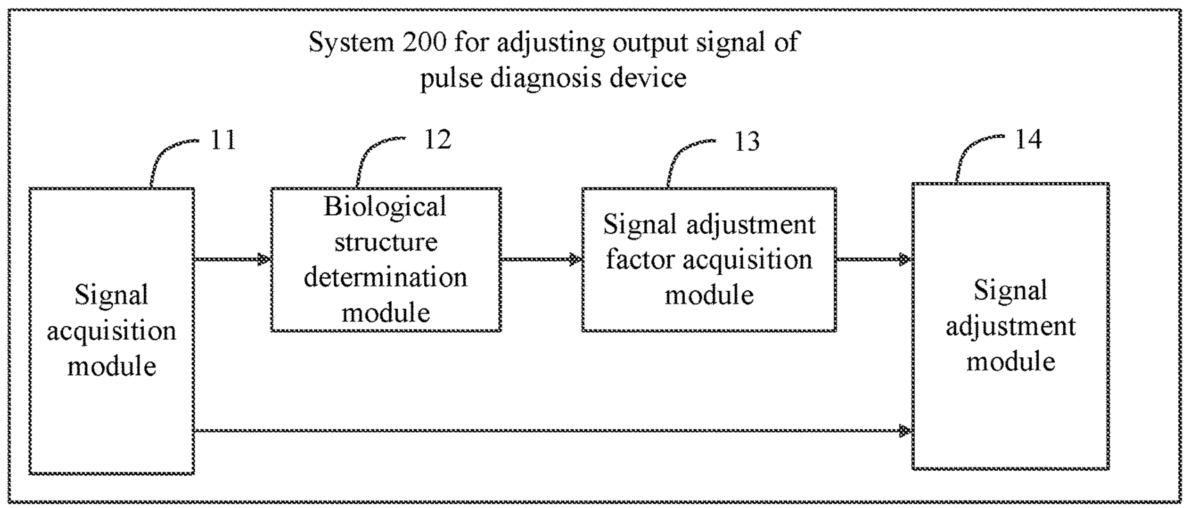
FIG. 11 is a modular structure of a system for adjusting the output signal of the pulse diagnosis device, according to an example embodiment of the present disclosure.

As shown in FIG. 11, the system 200 for adjusting the output signal of the pulse diagnosis device 10 may include a signal acquisition module 11, a biological structure determination module 12, a signal adjustment factor acquisition module 13, and a signal adjustment module 14. Although for simplicity, the processor 5 and the memory 6 are not shown in FIG. 11, a person having ordinary skills in the art can appreciate that the system 200 for adjusting the output signal of the pulse diagnosis device 10 may be a part of the processor 5 and/or the memory 6. For example, in some embodiments, one or more modules of the signal acquisition module 11, the biological structure determination module 12, the signal adjustment factor acquisition module 13, and the signal adjustment module 14 may be included as parts of the processor 5. In some embodiments, these modules may respectively correspond to one or more electrical circuits configured to process signals or data in the processor 5, or may correspond to relevant program instructions stored in the computer-readable medium (e.g., memory 6). In some embodiments, the signal acquisition module 11, the biological structure determination module 12, the signal adjustment factor acquisition module 13, and the signal adjustment module 14 may not be parts of the processor 5, but may be parts of another processor that is separately provided from processor 5. In some embodiments, one or more of the signal acquisition module 11, the biological structure determination module 12, the signal adjustment factor acquisition module 13, and the signal adjustment module 14 may be integrated as a single module. In some embodiments, the signal acquisition module 11 may be configured to obtain a pulse signal in a pulse diagnosis region acquired by a sensing element of the pulse diagnosis device 10. The biological structure determination module 12 may be configured to recognize at least one of the amplitude and pressure of the pulse signal, and to determine a biological structure in the pulse diagnosis region based on a recognition result of at least one of the amplitude and pressure. The signal adjustment factor acquisition module 13 may be configured to obtain an adjustment factor of a value of at least one of the amplitude and pressure of the pulse signal. The signal adjustment module 14 may be configured to adjust the value of at least one of the amplitude and pressure of the pulse signal based on the adjustment factor of the value of the at least one of the amplitude and pressure of the pulse signal, to obtain the adjusted pulse signal for the pulse diagnosis region.

Further, in some embodiments, the biological structure determination module 12 may be configured to determine the biological structure of the pulse diagnosis region based on the following method: based on a predetermined corresponding relationship between at least one of the amplitude samples and pressure samples and predetermined biological structures, matching to determine a corresponding biological structure based on a recognition result of at least one of the amplitude and pressure. Specifically, in some embodiments, the biological structure of the pulse diagnosis region may be a bone, a muscle, or a fat (or a combination of any of the two or three). A structural feature of the biological structure may include at least one of a location and a thickness of the biological structure in the pulse diagnosis region. For example, when the pulse diagnosis region is a radial artery region of a wrist of a human body, the structural feature of the biological structure of the radial artery region may include at least one of a location and a thickness of the bone, at least one of a location and a thickness of the muscle, or at least one of a location and a thickness of the fat, or any suitable combination thereof. More specifically, the corresponding relationship or mapping relationship between at least one of the amplitude and pressure and the biological structure may be pre-established through various methods, including, but not limited to, repeated experiments or simulation modeling. The former involves using a pulse diagnosis device (e.g., the pulse diagnosis device 10) to actually diagnose the pulses of different objects to be diagnosed or different parts of the wrist of a same object to be diagnosed, and to collect data of at least one of the detected amplitude and pressure. The collected data may be processed to remove noise. The data after noise is removed and the corresponding biological structures may be stored in the form of an inquiry table or a mapping table. In the latter situation, because there are differences in the conductivity of the pulse by different biological structures such as the bone, the muscle, and the fat, different simulation models may be established with respect to these differences. A predetermined artery pulse force may be applied to these simulation models, and a statistic analysis may be performed on the output results of the pulse signals of the various simulation models. A corresponding relationship between at least one of the amplitudes and pressures of these pulse signals and various simulation models may be saved in the form of an inquiry table or a mapping table. Regarding this aspect, a person having ordinary skills in the art can appreciate that the level of division of the simulation model is determined based on the expected accuracy of signal adjustment. The finer the division of the simulation model, the more accurately the simulation model corresponds to the various different biological structures. Correspondingly, the ultimate adjustment result of the pulse signal can be more accurate.

Further, in some embodiments, the signal adjustment factor acquisition module 13 may obtain the adjustment factor of the value of at least one of the amplitude and pressure of the pulse signal based on the following method: based on a predetermined corresponding relationship between predetermined biological structure samples and predetermined adjustment factors of values of at least one of the amplitude and pressure of the pulse signal, matching to determine the corresponding adjustment factor of the value of at least one of the amplitude and pressure of the pulse signal based on the biological structure of the pulse diagnosis region. That is, the biological structure determined by the biological structure determination module 12 may be used as an index to inquire the pre-established corresponding relationship or the mapping relationship between the biological structures and the adjustment factors of the values of at least one of the amplitudes and pressures of the pulse signals, to obtain the corresponding adjustment factor.

As described above, the corresponding relationship or the mapping relationship between the biological structures and the adjustment factors of the values of at least one of the amplitude and pressure of the pulse signal may be pre-established through various methods, including, but not limited to, repeated experiments or simulation modeling. For example, the former involves using a pulse diagnosis device (e.g., the pulse diagnosis device 10) to perform actual pulse diagnoses on objects to be diagnosed who have different biological shapes, to collect detected data of at least one of the amplitude and pressure. The collected data may be processed to remove noise. An adjustment factor for an object to be diagnosed having other biological structures may be calculated based on data of at least one of the amplitude and pressure of an object to be diagnosed having standard biological structures. Finally, the calculated adjustment factors and the corresponding biological structures may be stored in the form of an inquiry table or a mapping table.

In some embodiments, simulation modeling may be used to pre-establish the corresponding relationship or the mapping relationship between the biological structures and the adjustment factors of the values of at least one of the amplitude and pressure of the pulse signal. The detailed processes can refer to the descriptions in connection with FIG. 9, which are not repeated.

In addition, the system for adjusting the output signal of the pulse diagnosis device 10 may be configured to determine the center line of the radial artery, the Cun pulse location, the Guan pulse location, and the Chi pulse location based on specific methods, the details of which can refer to the above descriptions in connection with FIG. 10, which are not repeated.

In some embodiments, the system for adjusting the output signal of the pulse diagnosis device 10 as shown in FIG. 11 may be configured to execute the method for adjusting the output signal of the pulse diagnosis device 10 as shown in FIG. 8. The technical principles between the system and the method, the technical issues to be addressed and the technical effects realized are similar. A person having ordinary skills in the art can appreciate, that for the convenience of description, the detailed operation processes of the system 200 for adjusting the output signal of the pulse diagnosis device 10 and related descriptions can refer to the above described content regarding the embodiments of the method for adjusting the output signal of the pulse diagnosis device 10, which are not repeated.

Figure 12:
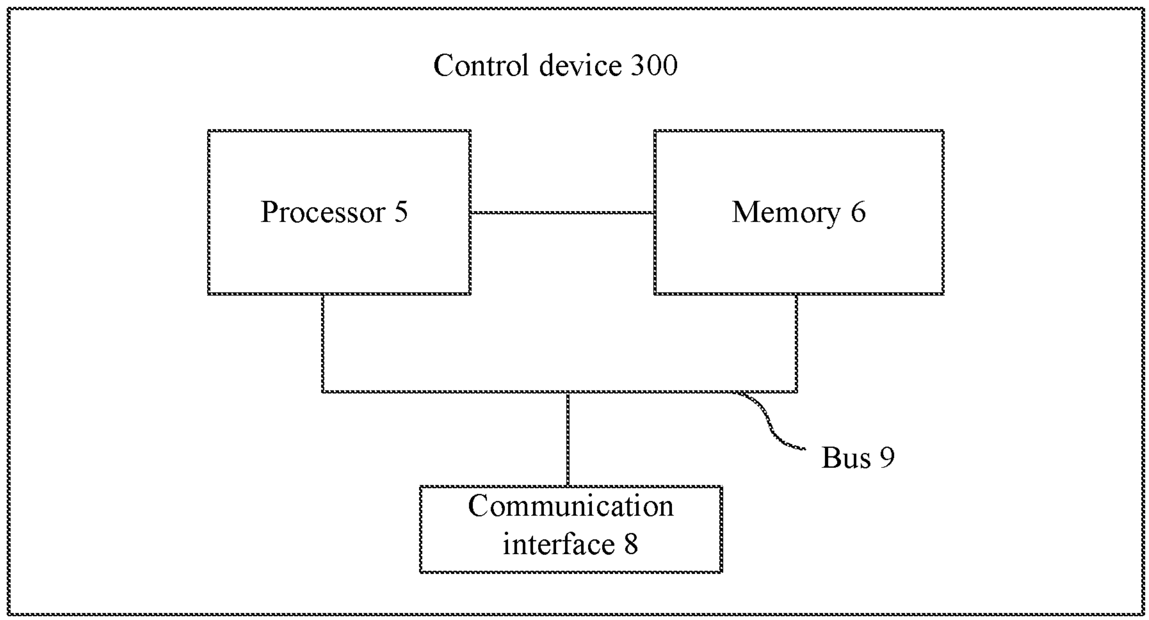
FIG. 12 is a schematic diagram of a structure of a control device, according to an embodiment of the present disclosure.

FIG. 12 is a schematic diagram of a structure of a control device 300. The control device 300 may be a portion of the pulse diagnosis device 10 shown in FIG. 1. In some embodiments, the control device 300 may not be a part of the pulse diagnosis device 10, but may be separate from the pulse diagnosis device 10 and be communicatively connected with the pulse diagnosis device 10. The control device 300 may include a processor, e.g., the processor 5, a memory, e.g., the memory 6, and a communication interface (or device) 8. The memory 6 may be configured to store program instructions or codes. The processor 5 may be configured to retrieve the program instructions and to execute the instructions to perform the disclosed methods. The communication interface 8 may be connected to the processor 5 and the memory 6 through a bus 9. The communication interface 8 may be configured to communicate with an external device disposed external to the control device 300 (e.g., data transmission). In some embodiments, the processor 5 may be connected to the memory 6 through the bus 9.

A person having ordinary skills in the art can appreciate, the various modules included in the system 200 for adjusting the output signal of the pulse diagnosis device 10 are functional units for describing the system. In practical applications, the adjustment system may be implemented in the form of a computer program that may be loaded and executed by the processor. The physical elements corresponding to these modules may be included in the processor, or may be a software portion of the processor, a hardware portion of the processor, or a combination of the software portion and the hardware portion of the processor. Specifically, in practical applications, the pulse diagnosis device 10 may include the processor 5 and the memory 6. The memory 6 may be configured to store the computer program. The processor 5 may be configured to load and execute the computer program to realize the system and method for adjusting the output signal of the pulse diagnosis device of the present disclosure. As an example, the memory may include, but not limited to, a random-access memory, a flash memory, a read-only memory, a programmable read only memory, a volatile memory, a non-volatile memory, a serial memory, a parallel memory, or a register, etc. The processor may include, but not limited to, CPLD/FPGA, DSP, ARM processor, MIPS processor, etc. In order not to affect the descriptions of the core principles of the present disclosure, such known structures may not have been shown in the figures.

Further, it should be understood that the configurations of the various modules are only for the purpose of describing the functional units of the system or device of the present disclosure. The physical elements corresponding to these modules may be parts of the processor, or may be the software portion of the processor, the hardware portion of the processor, or a combination of the software portion and hardware portion of the processor. Therefore, the quantity of the various modules shown in the figures are only illustrative. A person having ordinary skills in the art can appreciate that the various modules of the system may be suitably divided or integrated. The division or integration of specific modules does not cause the technical solution to deviation from the principles of the present disclosure. Therefore, the technical solutions after the division or integration all fall within the scope of protection of the present disclosure.

In addition, a person having ordinary skills in the art can appreciate, the present disclosure may be realized as a program executable by a device or apparatus to perform some or all of the described methods (e.g., a computer program or a computer program product). The program for realizing the present disclosure may be stored in a computer-readable storage medium, or may be in the form of one or more signals. Such signals may be downloaded from an Internet website, or be provided via a carrier signal, or be provided in any other suitable form.

The above described the technical solution of the present disclosure with reference to the embodiments shown in the figures. A person having ordinary skills in the art can appreciate that the scope of protection of the present disclosure is not limited to such detailed embodiments. Without deviating from the principle of the present disclosure, a person having ordinary skills in the art may perform equivalent modification or substitution for some related technical features. Technical solutions with such modification or substitution still fall within the scope of protection of the present disclosure.

What is claimed is:

1. A method for adjusting an output signal of a pulse diagnosis device, comprising:

applying, by a pressure applying device included in the pulse diagnosis device, an external pressure that linearly increases with time to a wrist;

while the external pressure is applied, acquiring, by a pressure sensor array included in the pulse diagnosis device, at a radial artery region of a radial artery of the wrist, a mixed pressure signal, wherein the mixed pressure signal is a mixed result of the applied external pressure and a pulse signal at the radial artery;

removing, by a low frequency filter included in the pulse diagnosis device, the external pressure from the mixed pressure signal to obtain the pulse signal;

performing, by a processor included in the pulse diagnosis device, a parameter recognition on the pulse signal to obtain an amplitude of the pulse signal;

determining, by the processor included in the pulse diagnosis device, a biological structure of the radial artery region based on the amplitude of the pulse signal;

determining, by the processor included in the pulse diagnosis device, an adjustment factor for the amplitude of the pulse signal based on the biological structure; and adjusting, by the processor included in the pulse diagnosis device, the amplitude of the pulse signal based on the adjustment factor, to obtain an adjusted pulse signal as the output signal of the pulse diagnosis device, wherein, the pulse signal is a pressure signal applied by the radial artery in the radial artery region to an external skin surface corresponding to the radial artery and acquired by the pressure sensor array.

2. The method for adjusting the output signal of the pulse diagnosis device according to claim 1, wherein determining the biological structure of the radial artery region based on the amplitude of the pulse signal comprises:

based on a predetermined corresponding relationship between predetermined parameter samples and predetermined biological structure samples, matching to determine the biological structure based on the amplitude of the pulse signal.

3. The method for adjusting the output signal of the pulse diagnosis device according to claim 1, wherein determining the adjustment factor for the amplitude of the pulse signal based on the biological structure comprises:

based on a predetermined corresponding relationship between predetermined biological structure samples and predetermined adjustment factors for the amplitude of the pulse signal, matching to determine the adjustment factor for the amplitude of the pulse signal based on the biological structure.

4. The method for adjusting the output signal of the pulse diagnosis device according to claim 1, wherein the biological structure comprises a bone, a muscle, a fat, or a combination thereof, and wherein a structural feature of the biological structure comprises at least one of a location and a thickness of the biological structure of the radial artery region.

5. The method for adjusting the output signal of the pulse diagnosis device according to claim 1, wherein the amplitude is an average value of amplitudes of multiple output signals of the pressure sensor array, or is a distribution parameter of the amplitudes of the multiple output signals of the pressure sensor array.

6. The method for adjusting the output signal of the pulse diagnosis device according to claim 1, wherein the amplitude is a maximum value of amplitudes of multiple output signals of the pressure sensor array.

7. The method for adjusting the output signal of the pulse diagnosis device according to claim 1, wherein the pressure sensor array includes a plurality of pressure sensors distributed in a plurality of rows, wherein the method further comprises:

determining, by the processor, a center line of the radial artery by:

obtaining a location of a pressure sensor that detects a largest pulse signal in each row in the pressure sensor array; and connecting a plurality of locations of the pressure sensors that detect the largest pulse signal in the rows to obtain the center line of the radial artery; and determining the radial artery region based on the center line of the radial artery for detecting the pulse signal.

8. A method for adjusting an output signal of a pulse diagnosis device, comprising:

applying, by a pressure applying device included in the pulse diagnosis device, an external pressure that linearly increases with time to a wrist;

while the external pressure is applied, acquiring, by a pressure sensor array included in the pulse diagnosis device, at a radial artery region of a radial artery of the wrist, a mixed pressure signal, wherein the mixed pressure signal is a mixed result of the applied external pressure and a pulse signal at the radial artery;

removing, by a low frequency filter included in the radial artery device, the external pressure from the mixed pressure signal to obtain the pulse signal;

performing, by a processor included in the pulse diagnosis device, a parameter recognition on the pulse signal to obtain an amplitude of the pulse signal;

based on a predetermined corresponding relationship between predetermined parameter samples and predetermined biological structure samples, matching, by the processor included in the pulse diagnosis device, to determine a corresponding biological structure based on the amplitude of the pulse signal;

based on a predetermined corresponding relationship between predetermined biological structure samples and predetermined adjustment factors for the amplitude of the pulse signal, matching, by the processor included in the pulse diagnosis device, to determine a corresponding adjustment factor for the amplitude of the pulse signal based on the biological structure; and adjusting, by the processor included in the pulse diagnosis device, the amplitude of the pulse signal based on the adjustment factor to obtain an adjusted pulse signal for the radial artery region, wherein, the pulse signal is a pressure signal applied by the radial artery in the radial artery region to an external skin surface corresponding to the radial artery and acquired by the pressure sensor array, and wherein the biological structure comprises a bone, a muscle, a fat, or a combination thereof, and a structural feature of the biological structure comprises at least one of a location and a thickness of the biological structure in the radial artery region.

9. A pulse diagnosis device, comprising:

a pressure applying device configured to apply an external pressure to a wrist, the external pressure being linearly increasing with time;

a pressure sensor array including a plurality of pressure sensors configured to acquire, while the external pressure is applied, a mixed pressure signal at a radial artery region of a radial artery of the wrist, the mixed pressure signal being a mixed result of the applied external pressure and a pulse signal at the radial artery;

a processor configured to:

remove the external pressure from the mixed pressure signal to obtain the pulse signal;

perform a parameter recognition on the pulse signal to obtain an amplitude of the pulse signal, and to determine a biological structure of the radial artery region based on the amplitude of the pulse signal;

obtain an adjustment factor for the amplitude of the pulse signal based on the biological structure; and adjust the amplitude of the pulse signal based on the adjustment factor for the amplitude of the pulse signal, to obtain an adjusted pulse signal for the radial artery region, wherein, the pulse signal is a pressure signal applied by the radial artery in the radial artery region to an external skin surface corresponding to the radial artery and acquired by the pressure sensor array.

10. The pulse diagnosis device according to claim 9, wherein the processor is configured to determine the biological structure of the radial artery region by:

based on a predetermined corresponding relationship between predetermined parameter samples and predetermined biological structures, matching to determine a structural feature of the biological structure based on the amplitude of the pulse signal.

11. The pulse diagnosis device according to claim 9, wherein the processor is configured to obtain the adjustment factor for the amplitude of the pulse signal by:

based on a predetermined corresponding relationship between predetermined biological structure samples and predetermined adjustment factors for the amplitude of the pulse signal, matching to determine the adjustment factor for the amplitude of the pulse signal based on the biological structure.

12. The pulse diagnosis device according to claim 9, wherein the biological structure comprises a bone, a muscle, a fat, or a combination thereof, and wherein a structural feature of the biological structure comprises at least one of a location and a thickness of the biological structure of the radial artery region.

13. The pulse diagnosis device according to claim 9, wherein the amplitude is an average value of amplitudes of multiple output signals of the pressure sensor array, or is a distribution parameter of the amplitudes of the multiple output signals of the pressure sensor array.

14. The pulse diagnosis device according to claim 9, wherein the amplitude a maximum value of amplitudes of multiple output signals of the pressure sensor array.

15. The pulse diagnosis device according to claim 9:

wherein the processor is configured to determine the biological structure also based on a predetermined corresponding relationship between predetermined parameter samples and predetermined biological structure samples, wherein the processor is configured to obtain the adjustment factor for the amplitude of the pulse signal also based on a predetermined corresponding relationship between predetermined biological structure samples and predetermined adjustment factors for the amplitude of the pulse signal, and wherein the biological structure includes a bone, a muscle, a fat, or a combination thereof, and a structural feature of the biological structure includes at least one of a location and a thickness of the biological structure in the radial artery region.

* * * * *